United States Patent
Bhattacharya

(10) Patent No.: US 10,588,582 B2
(45) Date of Patent: Mar. 17, 2020

(54) CROSS-CALIBRATION FOR QUANTITATIVE FUNCTIONAL IMAGING

(71) Applicant: Siemens Medical Solutions USA, Inc., Malvern, PA (US)

(72) Inventor: Manojeet Bhattacharya, Chicago, IL (US)

(73) Assignee: Siemens Medical Solutions USA, Inc., Malvern, PA (US)

(*) Notice: Subject to any disclaimer, the term of this patent is extended or adjusted under 35 U.S.C. 154(b) by 225 days.

(21) Appl. No.: 15/831,445

(22) Filed: Dec. 5, 2017

(65) Prior Publication Data

US 2018/0092609 A1    Apr. 5, 2018

Related U.S. Application Data

(62) Division of application No. 14/595,254, filed on Jan. 13, 2015, now Pat. No. 9,867,581.

(60) Provisional application No. 61/927,198, filed on Jan. 14, 2014.

(51) Int. Cl.
*A61B 6/03* (2006.01)
*A61B 6/00* (2006.01)

(52) U.S. Cl.
CPC ............. *A61B 6/037* (2013.01); *A61B 6/582* (2013.01); *A61B 6/4258* (2013.01); *A61B 6/461* (2013.01); *A61B 6/52* (2013.01)

(58) Field of Classification Search
CPC ........... A61B 6/582; A61B 6/037; A61B 6/52; A61B 6/461; A61B 6/4258
See application file for complete search history.

(56) References Cited

U.S. PATENT DOCUMENTS

| | | | |
|---|---|---|---|
| 5,491,342 A | 2/1996 | Lim et al. | |
| 9,364,192 B2 | 6/2016 | Vija | |
| 9,504,431 B2 | 11/2016 | Bhatttacharya | |
| 2008/0042067 A1* | 2/2008 | Rousso | A61B 5/417 250/363.04 |
| 2009/0127449 A1 | 5/2009 | Iwatschenko-Borho | |
| 2014/0371580 A1 | 12/2014 | Bhattacharya | |

OTHER PUBLICATIONS

"Quality Assurance for SPECT Systems," IAEA Human Health Series, No. 6, International Atomic Energy Agency, Vienna, pp. 1-263, 2009.
Larsson, Anne, "Corrections for improved quantitative accuracy in SPECT and planar scintigraphic imaging," Department of Radiation Sciences, Radiation Physics, Umea University, Sweden, pp. 1-88, 2005.

* cited by examiner

*Primary Examiner* — Bo Joseph Peng

(57) ABSTRACT

Cross-calibration is provided for functional imaging. In PET or SPECT, the inaccuracies from the dose and detector sensitivity may be reduced or removed in both activity concentration and uptake. By using measures from both the radiotracer for the patient and factory calibrated sources, the variability due to dose may be removed. In SPECT, a measurement of system specific sensitivity to a factory calibrated point source is used to improve the accuracy of uptake values, not just activity concentration.

8 Claims, 2 Drawing Sheets

CROSS-CALIBRATION FOR QUANTITATIVE FUNCTIONAL IMAGING

RELATED APPLICATIONS

The present patent document is a divisional application of U.S. patent application Ser. No. 14/595,254, filed Jan. 13, 2015, which claims the benefit of the filing date under 35 U.S.C. § 119(e) of Provisional U.S. Patent Application No. 61/927,198, filed Jan. 14, 2014, which is hereby incorporated by reference.

BACKGROUND

The present embodiments relate to calibration for functional imaging. Calibration is provided for quantitative functional imaging.

Functional imaging uses a radioisotope or radiotracer to determine metabolic function within a patient. For example, the uptake of the radiotracer by tissues in the body is measured. Positron emission tomography (PET) and single photon emission computed tomography (SPECT) are two types of functional imaging. The emissions from the radiotracer are detected in the functional imaging. The activity concentration (i.e., the concentration of the radiotracer from different locations) is reconstructed from the detected emissions.

The reconstruction uses the sensitivity of the detector for the emissions. This sensitivity may be calibrated, but contributes a possible source of error in quantitative functional imaging. If a class standard sensitivity is used, the detector specific sensitivity may be different. Similarly, the dose applied to the patient introduces another source of error in quantitative functional imaging. The dose value for the liquid isotope applied to the patient may be inaccurate.

For quantitative functional imaging, both accurate activity concentration and uptake values are desired. The goal is to provide a global baseline that is free of system (detector and dose calibrator) variability so that any measured change for a patient over time in either quantity is due to metabolic reasons. Clinically useable cross-calibration accounting for detector sensitivity and dose sensitivity in SPECT has been problematic because the incompatibility of isotropic point sources made with liquid radiotracers and anisotropic factory-calibrated sealed sources with long-lived isotopes. Scaling the class standard gamma camera planar sensitivity for emission energy of a given radiotracer with the system specific sensitivity measured using factory calibrated sealed point sources having emission energies close to the emission energies of the radiotracer for the patient may produce activity concentrations that are accurate at the expense of inaccurate uptake values. On the other hand, scaling the class standard gamma camera planar sensitivity using system specific sensitivity measured with a locally made point source of the radiotracer for the patient may produce accurate uptake values but inaccurate activity concentrations.

BRIEF SUMMARY

By way of introduction, the preferred embodiments described below include methods, systems, and non-transitory computer readable media for cross-calibration for functional imaging. In PET or SPECT, the inaccuracies from the injected dose and detector sensitivity may be reduced or removed in both activity concentration and uptake. By using measures from both the radiotracer for the patient and factory calibrated sources, the variability due to dose may be removed. In SPECT, a measurement of system specific sensitivity to a factory calibrated point source is used to improve the accuracy of uptake values, not just activity concentration.

In a first aspect, a method is provided for cross-calibration for quantitative single photon emission computed tomography (SPECT). Class standard planar sensitivities of a gamma camera class to a first long-lived source and to a first liquid radiotracer source are obtained. A system specific planar sensitivity of a gamma camera of the gamma camera class to a second long-lived source is measured. A dose calibrator referenced liquid radiotracer sensitivity of a second liquid radiotracer is measured. A system specific planar sensitivity to the second liquid radiotracer is calculated as a function of the class standard planar sensitivities of the gamma camera to the first liquid radiotracer source and the first long-lived source and of the system specific planar sensitivity of the gamma camera to the second long-lived source. A cross-calibration factor is determined as a function of the system specific planar sensitivity to the second liquid radiotracer and of the liquid radiotracer sensitivity. A dose value of the second liquid radiotracer is corrected with the cross-calibration factor. Activity concentration in a patient having the second liquid radiotracer is estimated. The estimating is part of reconstruction using the system specific planar sensitivity.

In a second aspect, a non-transitory computer readable storage medium has stored therein data representing instructions executable by a programmed processor for cross-calibration in single photon emission computed tomography (SPECT). The storage medium includes instructions for: measuring a system specific sensitivity of a camera to a long-lived point source; estimating activity concentration in SPECT as a function of the system specific sensitivity; correcting an injected dose value as a function of the system specific sensitivity; and calculating a specific uptake value from the activity concentration and the corrected injected dose value.

In a third aspect, a system is provided for cross-calibration in functional imaging quantification. A functional imaging system has a detector. A calibration radiotracer source is provided. A processor is configured to reduce variability due to dose and detector sensitivity of uptake values output by the functional imaging system for a patient. The processor is configured to reduce variability as a function of a class standard sensitivity to a liquid radiotracer source and a system specific sensitivity to the calibration radiotracer source.

The present invention is defined by the following claims, and nothing in this section should be taken as a limitation on those claims. Further aspects and advantages of the invention are discussed below in conjunction with the preferred embodiments and may be later claimed independently or in combination.

BRIEF DESCRIPTION OF THE DRAWINGS

The components and the figures are not necessarily to scale, emphasis instead being placed upon illustrating the principles of the invention. Moreover, in the figures, like reference numerals designate corresponding parts throughout the different views.

DETAILED DESCRIPTION OF THE DRAWINGS AND PRESENTLY PREFERRED EMBODIMENTS

Rather than including inaccuracy from liquid radioisotope measures, a system specific sensitivity of the detector to a factory calibrated long-lived point source is measured and used to calculate sensitivity of the detector to the liquid radioisotope. A ratio of class standard sensitivities for long lived and liquid radioisotopes is used with the measured system specific sensitivity to a factory calibrated long-lived point source to calculate the system specific sensitivity to the liquid radioisotope. A cross-calibration factor for correcting the injected dose of liquid radioisotope is a ratio of the calculated system specific sensitivity to the liquid radioisotope and a measured liquid radioisotope sensitivity referenced to the dose calibrator. The calculated system specific sensitivity to the liquid radioisotope is used in reconstruction of the activity concentration, providing accurate activity concentration despite variability in the dose. The corrected dose and activity concentration are used to quantify accurate uptake despite the use of class standards.

This approach provides global as well as local baselines by eliminating both camera and dose calibrator variability. Different quantitative measures for a patient at different times and/or with different functional imaging systems are comparable. The quantitative evaluation is comparable across populations or between patients, assisting in diagnosis and/or therapy for a given patient. Any changes over time are more likely due to change in function rather than detector or dose variance.

Figure 1:
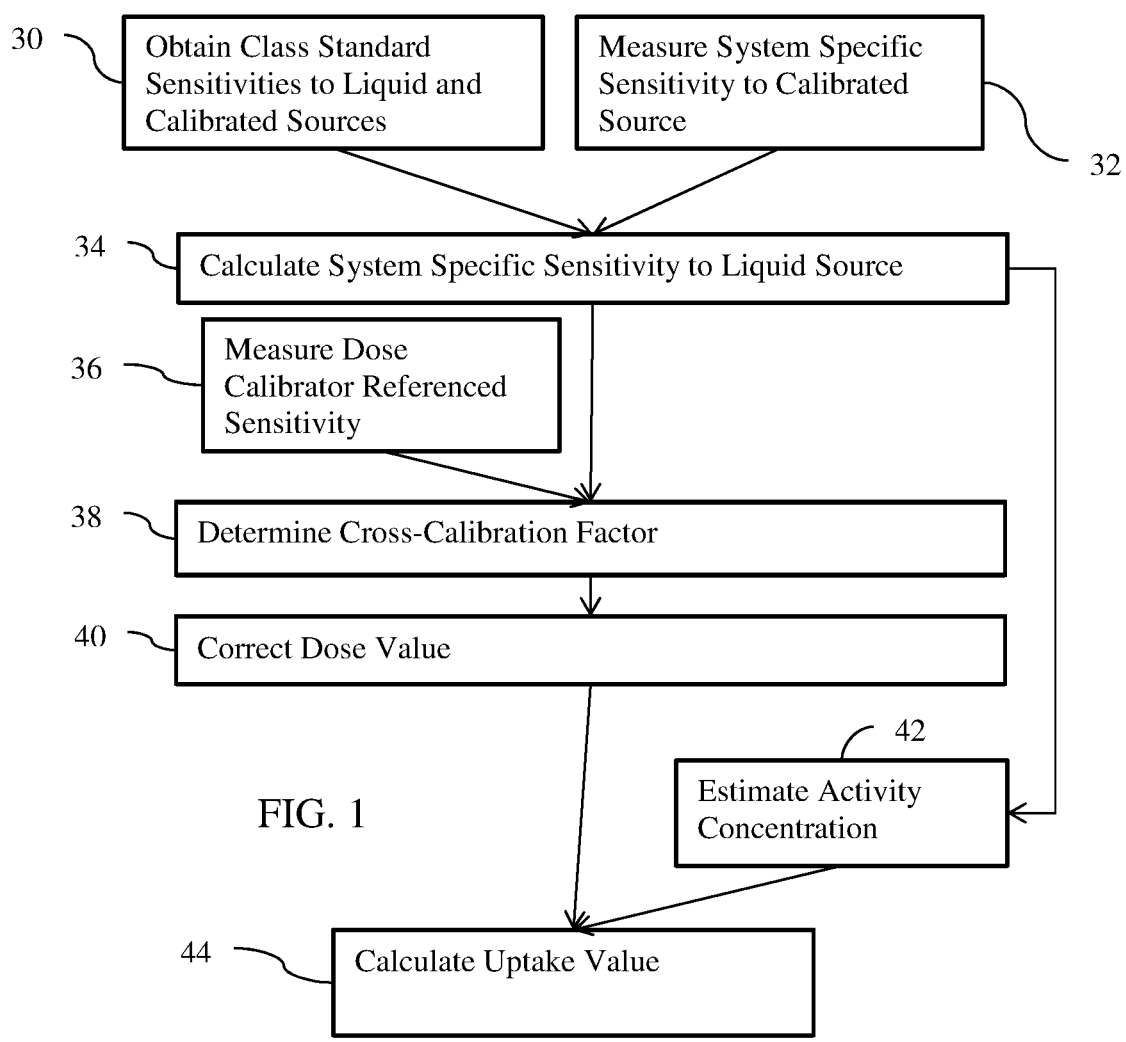
FIG. 1 is a flow chart diagram of one embodiment of a method for cross-calibration in functional imaging.

FIG. 1 shows one embodiment of a method for cross-calibration in quantitative single photon emission computed tomography (SPECT) or positron emission tomography (PET). Other functional imaging may be used. For activity concentration estimation or uptake calculation (e.g., specific uptake value calculation), the dose and detector sensitivity are calibrated in a way removing variability due to both dose and detector. The examples below are provided for SPECT, but may be used in PET or other functional imaging modality.

The method is applied for a given scan of a given patient. By applying the method to different scans of the patient, the resulting quantities may be compared and have little to no variance due to differences in dose and detector. The different scans use the same or different detectors and/or doses. Similarly, the quantities may be compared between patients to establish norms or deviation from norm. Without the cross-calibration, comparison of activity concentration or uptake over time, detectors, doses, and/or patients is subject to variance unrelated to the metabolic function of the patient or patients.

Additional, different, or fewer acts may be performed. For example, acts 36-40 are not provided. As another example, acts 42 and/or 44 are not provided. In other examples, acts related to positioning the patient, configuring the SPECT scanner, and/or SPECT imaging are provided.

The acts are performed in the order shown or a different order. For example, act 36 is performed prior to act 34. As another example, act 42 is performed before act 40, 38, and/or 36. Acts 30 and 32 may be performed in any order.

In act 30, class standard sensitivities of the detector are obtained. The sensitivities are obtained by loading from memory, transfer, and/or measurements.

For SPECT, the sensitivities are planar sensitivities of a gamma camera class. The detectors include photomultiplier tubes or other photon detectors layered with a scintillation crystal. The photomultiplier tubes are arranged along a rectangular or other grid to provide a two-dimensional planar array for detecting gamma radiation. Other types of detectors may be used, such as a ring of detectors in PET.

Any class or grouping may be used, such as defining a class as a given construction (e.g., materials and array configuration) with or without a specific collimator and/or scintillator crystals. For a given class, a number of different gamma cameras are manufactured to be used in a respective number of different SPECT systems. Different types of SPECT systems may use the same or different class of detectors.

The class of detectors has a class sensitivity to radiation sources. Different classes have different sensitivities. Within a class, given detectors may have different sensitivities, but generally have similar sensitivities. For a class sensitivity, the average sensitivity is calculated from measurements by any number (e.g., tens or hundreds) of members of the class.

To determine the class standard sensitivity, a point or other source of gamma radiation is positioned at a fixed distance (e.g., 20 cm) from the detectors. Counts of detected gamma photons are collected by the detectors. The time from the first count to a given number of counts is determined. The sensitivity is the number of counts divided by the time and the dose of the source. Other calculations of sensitivity may be used.

Class standard (CS) sensitivity, $S_{LL}(CS)$, is measured for a factory calibrated long-lived (LL) point source. Any size point source may be used, such as 1 $mm^3$. The long-lived or factory calibrated point source has a known dosage that is precise. Any amount of precision or tolerance may be provided, such as being more precise (e.g., by a factor of 10) than of a dose of a lab provided liquid radiotracer.

Class standard sensitivity, $S_{LR}(CS)$, is also measured for a liquid radiotracer (LR). The liquid radiotracer is encased in a sphere or other phantom to act as a point source. The detector sensitivity to the liquid radiotracer is measured by the various detectors and averaged. For determining a class standard, different batches of the radiotracer may be provided at different times to measure with all members of the group of detectors of the testing class. Alternatively, one batch is used for all of the class standard sensitivity measurements. Since the dose of the liquid radiotracer has more variability or is less precise, the resulting class standard sensitivity for the liquid radiotracer may be less precise than the class standard sensitivity for the long-lasting point source.

Any radiotracer may be used, such as 99Tc. The class standard sensitivity for the long-lived point source has a dose that is close (e.g., within 10%) or the same as for the liquid radiotracer. The class standard sensitivities for the liquid radiotracer are for the same radiotracer to be used for patient examination. For example, different class standard sensitivities are obtained for different radiotracers. Alternatively, the class standard for the liquid radiotracer is a different radiotracer than used for examining a patient.

In act 32, a system specific sensitivity, $S_{LL}(SS)$, of a detector to a long-lived point source is measured using the detector, a timer, and processor. For a given SPECT system, the planar gamma camera is used to measure sensitivity. The sensitivity of the specific SPECT system gamma camera of the class of cameras is measured.

The same or different long-lived point source used for determining the class standard is used. For example, a technician periodically maintains or calibrates a given SPECT system at a medical institution. As part of the maintenance, the system specific sensitivity to a long-lived point source provided and positioned by the technician is measured. This is a different point source than used for the class standard measurements used by others at a testing lab, manufacturing facility, or other medical institutions. In another example, the system specific sensitivity to the long-lived or factory calibrated point source is measured after manufacture but before providing to the medical institution. The same point source used for the class is used. Alternatively, a different point source with the same or similar (e.g., within 10%) dose in Becquerel is used. Due to the factory calibration of the long-lived point source, the same calibration accuracy, independent of the site dose calibrator, is provided. In yet other embodiments, the point source used has a difference in energy greater than 10% from the point source used in the class standard measurements. Using a known dose provided with the precision of factory calibration, the sensitivity of the gamma camera is measured with less variability as compared to measurements from liquid radiotracers.

The same or different sensitivity measure is used for the system specific sensitivity as for the class standard. For example, the time to reach a given number of counts with the dose known for the point source is used. The number of counts used in both the class standard and system specific measurements is the same or different.

In act 34, a system specific sensitivity, $S_{LR}(SS)$, to a liquid radiotracer is calculated. Rather than measuring the system specific sensitivity using the liquid radiotracer to be injected into a patient, a processor calculates the system specific sensitivity. For SPECT, the system specific sensitivity is a planar sensitivity of a gamma camera. Placing the radiotracer in a phantom or point source container may be avoided. Instead, the sensitivity of the specific detector is calculated using various other information, such as the class standard sensitivity to a radiotracer with the same or similar energy or dose in Becquerel.

The system specific sensitivity to the liquid radiotracer is calculated using the class standard sensitivities of the detector class (e.g., type of planar gamma camera class) to the liquid radiotracer source and the long-lived source of act 30. The system specific sensitivity of the detector (e.g., gamma camera) to the long-lived source measured in act 32 is also used in calculating the system specific sensitivity to the liquid tracer. In one embodiment, the system specific sensitivity is calculated as a result of a (1) product of the class standard planar sensitivity to the liquid radiotracer source with the system specific planar sensitivity to the long-lived source being (2) divided by the class standard planar sensitivity to the long-lived source. This function is represented as:

$$S_{LR}(SS)=(S_{LR}(CS) \times S_{LL}(SS))/S_{LL}(CS).$$

The ratio of the class standard sensitivities for liquid and long-lived sources is assumed to be the same as the ratio of system specific sensitivities for liquid and long-lived sources. Since the precise system sensitivity to the long-lived source is measured in act 32, the liquid radiotracer sensitivity is derived by the processor. Reliance of the dose calibration accuracy for the liquid radiotracer is avoided. Other functions with or without constants or different mathematical operations may be used.

In act 36, a dose calibrator referenced liquid radiotracer sensitivity, $S_{LR}(XC)$, is measured and received. The processor receives the dose value from user input, loading from memory, or network transfer. In one embodiment, the dose calibrator referenced sensitivity is measured using a local dose calibrator and the gamma camera. For example, the dose calibrator referenced liquid radiotracer sensitivity is measured as disclosed in U.S. Published Application No. 2014/0371580. A detector of a gamma camera is configured such that a radioactive point source is positioned within a field of view at a fixed distance from the detector. A predetermined number of gamma photons emitted by the point source and passed through a collimator are acquired. A system-specific planar sensitivity is computed for a combination of the collimator and detector using the number of gamma photons acquired, a time duration of the acquisition, and precalibrated radioactivity data of the point source corrected for decay that occurred after a precalibration time. A deviation of the computed system-specific planar sensitivity from a class standard sensitivity value for a combination of the radioactive point source, the collimator, and the detector is computed. A class standard sensitivity value for a combination of a radiopharmaceutical, the collimator, and the detector is scaled by the computed deviation, yielding a scaled system-specific sensitivity value for the radiopharmaceutical. Other approaches may be used, such as measuring a ratio of observed counts to number of disintegrations in the radioactive source of a dose calibrator. This measurement is received by the acquisition computer.

The lab providing the liquid radiotracer to inject into the patient provides dose, such as a value in Becquerel. This dose is of the same type of liquid radiotracer used for the class standard sensitivity measurements, but may be of a different type of radiotracer. The lab provides the dose value of the liquid radiotracer measured using the local dose calibrator.

In act 38, a cross-calibration factor, $F_{xc}$, is determined. The cross-calibration factor accounts for both the detector sensitivity and the dose or liquid radiotracer sensitivity. The dose calibrator referenced liquid radiotracer sensitivity, $S_{LR}(XC)$, of the liquid radiotracer to be injected into the patient and the system specific planar sensitivity to the liquid radiotracer are combined as a cross-calibration function. Both the calibration for the dose and the calibration for the system specific detector are used. Other terms may be used.

In one embodiment, the cross-calibration factor is a ratio. The system specific planar sensitivity to the liquid radiotracer is divided by the dose calibrator referenced liquid radiotracer sensitivity, as represented by:

$$F_{xc}=S_{LR}(SS)/S_{LR}(XC)$$

This function provides a ratio of measured to derived sensitivity. The cross-calibration value is a function of a system specific sensitivity to a patient specific radiotracer calculated from the system specific sensitivity to the long-lived point source and a dose calibrator referenced radiotracer sensitivity. Other functions may be used.

In act 40, a dose value is corrected by the processor. The dose value is of the liquid radiotracer to be injected into the patient. The lab providing the radiotracer provides the dose, such as a value in Becquerel. The dose value is used in calculating uptake from the activity concentration. Prior to such use, the dose value is corrected using the cross calibration factor.

The dose value is corrected with the cross-calibration factor. Since the cross-calibration factor includes the system specific sensitivity to the long-lived point source through the calculation of the system specific sensitivity to the liquid radiotracer, the correction is a function of the system specific sensitivity of the factory calibrated, long-lived point source.

Correcting the injected dose by $F_{xc}$ may result in accurate uptake values free of either camera specific or local dose calibrator specific variations. Variations due to potentially asynchronous clocks between the camera system and the dose calibrator may be removed by the correction.

For correction, the cross-calibration factor is used directly. For example, the dose value is multiplied by or with the cross-calibration value. Other functions may be used. In alternative embodiments, the cross-calibration factor is used to look-up a weight or other adjustment applied to the dose value. In either the direct or indirect sense, the injected dose value for a radiotracer used in a patient is corrected with the cross-calibration value.

In act 42, the activity concentration is estimated. The activity concentration in a patient having received the liquid radiotracer is determined as part of reconstruction by the functional imaging system. After ingesting or injecting the radiotracer into the patient, the patient is positioned relative to the detector and/or the detector is positioned relative to the patient. Emissions from the radiotracer within the patient are detected over time. To determine the locations within the patient at which the emissions occurred, the detected emissions are reconstructed into an object space.

For reconstruction, the activity concentration (e.g., quantitative SPECT) is reconstructed using a system matrix. Distribution of emissions in a volume or image data is reconstructed from the detected emissions. The quantity or amount of uptake for each location (e.g., voxel) is estimated as part of the reconstruction in computed tomography. The SPECT imaging system estimates the activity concentration of an injected radiopharmaceutical or tracer for the different locations. In quantitative SPECT, the goal is to estimate the activity concentration in kBq/ml of the tracer (i.e., isotope) that was injected into and distributed within the patient.

The reconstruction is iterative and contains a model of the imaging formation physics as a pre-requisite of quantitative reconstruction. The image formation model includes the detected data (e.g., counts), the system matrix, isotope properties (e.g., corrected dose value), and biology. The system matrix represents mechanical properties of system, but may include other information (e.g., injection time and patient weight as represented by SUV).

Reconstruction includes a projection operator that is able to simulate a given SPECT system or SPECT class. Any now known or later developed reconstruction methods may be used, such as based on Maximum Likelihood Expectation Maximization (ML-EM), Ordered Subset Expectation Maximization (OSEM), penalized weighted least squares (PWLS), Maximum A Posteriori (MAP), multi-modal reconstruction, NNLS, or another approach.

The reconstruction uses the system matrix representing various aspects of the detection of the emissions, including modeling the imaging physics. The imaging physics includes aspects of the SPECT system, such as calibration of the SPECT system. The system matrix includes the detector sensitivity, such as the system specific sensitivity to the liquid radiotracer used in the patient. The system specific sensitivity (e.g., gamma camera planar sensitivity in SPECT) is used in the estimation of the activity concentration. The system specific sensitivity to the liquid radiotracer calculated in act 34 is used. Accordingly, the estimation is a function of the class standard sensitivities of act 30 and the measured system specific sensitivity to the calibrated or long-lived source of act 32. The corrected dose is included as part of the system matrix or as a separate isotope data used in reconstruction.

Using $S_{LR}(SS)$ for activity concentration estimation by the reconstruction engine may produce activity concentrations that are accurate and free of or less responsive to camera specific or local dose calibrator specific variations. The reconstructed activity concentrations may be free or be less responsive to asynchronous clocks between the camera system and the dose calibrator.

In act 44, specific uptake values (SUVs) are calculated by the processor of the functional imaging system. The activity concentration represents the amount of uptake at each location. This amount of uptake is a measure of emitted radiation, so is not normalized for the radiation dose provided to the patient. As a result, comparing uptake from different times may not be useful unless the same does is provided. By calculating the SUV, uptake normalized for dose is provided, allowing comparison of different measures.

The SUV for each location or for some of the locations is calculated. The SUV is a function of the activity concentration for that location and the corrected dose value from act 40. The activity concentration is divided by the corrected injected dose value. Other functions may be used. For example, the SUV may be a function of the body mass or other physical characteristic of the patient. The uptake magnitude represented in the activity concentration is normalized for both dose and body mass.

Due to the cross-calibration, measurement of the system specific sensitivity to the calibrated, long-lived source, and use of measurements from both the long-lived and liquid radiotracer sources, the SUV may be compared over time or from different examinations. Different radiotracer dose and/ or different detectors may be used. Where the different examinations use the approach of FIG. 1, the resulting difference in SUVs represents diagnostic or metabolic difference rather than difference due to variance in detector or dose. Quantification in functional imaging, such as SPECT, provides both accurate activity concentration and accurate SUVs.

Figure 2:
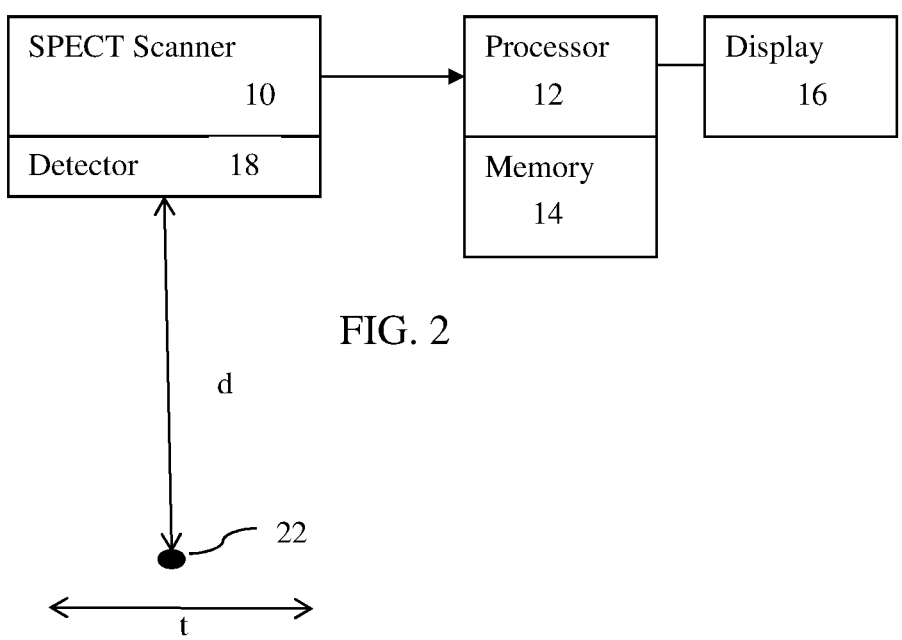
FIG. 2 is a block diagram of a system, according to one embodiment, for cross-calibration in functional imaging.

FIG. 2 shows a system 10 for cross-calibration in functional imaging. The system 10 includes an SPECT scanner 10, a processor 12, a memory 14, and a display 16. The processor 12, memory 14, and/or display 16 are part of the SPECT scanner 10 or are separate (e.g., a computer or workstation). Additional, different, or fewer components may be provided. For example, the system is a computer without the SPECT scanner 10. As another example, user input, patient bed, or other SPECT related devices are provided. Other parts of the system may include power supplies, communications systems, and user interface systems. In yet another example, a PET scanner or other functional imaging system is provided instead of the SPECT scanner 10.

The SPECT scanner 10 is a SPECT system. As a SPECT system, a detector 18 is provided. Other components may be provided, such as collimator. Any now known or later developed SPECT scanner 10 may be used.

The detector 18 is a gamma camera connected with a gantry. The gamma camera is a planar photon detector, such as having crystals or scintillators with photomultiplier tubes or other optical detector. The gantry rotates the gamma camera about the patient. During scanning of a patient, emission events are detected with the camera at different positions or angles relative to the patient. For sensitivity measurements from a point source 22 at a distance d from the detector 18, the gamma camera may be stationary.

The SPECT scanner 10, using the detector 18, detects emissions from the point source 22 for measuring system specific sensitivity. The point source 22 may be at any position in the 2D transverse direction, t, relative to the detector 18, but is preferably centered. The emissions are measured with the point source 22 at any distance, d.

The point source 22 is a long-lived, factory calibrated point source. Any size point source may be used, such as a 1 mm$^3$ vessel, with the long-lived radioisotope. The dose of the point source 22 is known with any degree of accuracy. The dose is measured at a factory with equipment having greater accuracy than used in labs providing liquid radiotracers. Any now known or later developed point source may be used. The point source 22 is used as a calibration radiotracer source. The long-lived point source 22 is for calibrating. The point source 22 is positioned relative to the detector 18 for measuring detector or system specific sensitivity to the point source.

The SPECT scanner 10 may include a timer. The timer measures a period from activation of detection through to reaching a number of counts. The emission events detected by the detector 18 are counted over time to calculate the sensitivity. The SPECT scanner 10, using the processor 12 or another processor, is configured to measure the system specific sensitivity of the detector 18 to the long-lived point source 22.

For imaging uptake in a patient, the detector 18 detects emissions from the patient. The emissions occur from any location in a finite source (i.e., the patient). The radiotracer in the patient migrates to, connects with, or otherwise concentrates at specific types of tissue or locations associated with specific biochemical reactions. As a result, a greater number of emissions occur from locations of that type of tissue or reaction. For example, the radiotracer is designed to link with locations of glucose uptake, fatty acid synthesis, or other metabolic process.

The SPECT scanner 10, using the processor 12 or another processor, is configured to reconstruct the imaged volume by applying a system matrix to the detected data. Any reconstruction may be used to estimate the activity concentration in the patient. The processor 12 is used to perform the reconstruction, or the SPECT scanner 10 has another processor that performs the reconstruction. The SPECT scanner 10 accesses the detected emission events from the memory 14 or buffers to reconstruct. The system matrix includes a system specific sensitivity for the liquid radiotracer provided to the patient. This sensitivity is used for the reconstruction. The reconstruction also uses a dose value for the radiotracer applied to the patient.

The processor 12 is a general processor, digital signal processor, graphics processing unit, application specific integrated circuit, field programmable gate array, digital circuit, analog circuit, combinations thereof, or other now known or later developed device for processing emission information. The processor 12 is a single device, a plurality of devices, or a network. For more than one device, parallel or sequential division of processing may be used. Different devices making up the processor 12 may perform different functions, such as one processor (e.g., application specific integrated circuit or field programmable gate array) for reconstructing and another for calculating a cross-calibration function and/or system specific sensitivity to a radiotracer to be injected. In one embodiment, the processor 12 is a control processor or other processor of SPECT scanner 10. In other embodiments, the processor 12 is part of a separate workstation or computer.

The processor 12 operates pursuant to stored instructions to perform various acts described herein, such as calculating of act 34, counting or controlling the counting and calculation of the system specific sensitivity to the point source 22 for the measurement of act 32, receiving the dose calibrator sensitivity in act 36, determining the cross-calibration factor of act 38, correcting the dose of act 40, estimating activity concentration of act 42, and/or calculating uptake values of act 44. The processor 12 is configured by software and/or hardware to perform, control performance, and/or receive data resulting from any or all of the acts of FIG. 1.

In one embodiment, the processor 12 is configured to reduce variability due to dose and detector sensitivity of uptake values and activity concentration output by the functional imaging system (e.g., the SPECT scanner 10) for a patient. The processor 12 is configured to reduce variability as a function of a class standard sensitivity to a liquid radiotracer source and a system specific sensitivity to the calibration radiotracer point source 22. The class standard sensitivities to a liquid radiotracer and to a long-lived point source are loaded from memory 14 or received by transfer. These sensitivities provide a ratio that may be used with the measured system specific sensitivity to a same or different point source 22 for calculating, by the processor 12, the system specific sensitivity to the liquid radiotracer. Using dose calibrator liquid radiotracer sensitivity, the processor 12 is configured to calculate a cross-calibration or dose correction factor. The sensitivity is input to the processor 12 with user interface, loaded from memory 14, or transferred over a network. The correction factor and calculated system specific sensitivity may reduce variability in reconstruction and/or calculation of specific uptake values.

The processor 12 is configured to correct the input dose of the liquid radiotracer provided to the patient. The correction factor is multiplied with the dose. Based on this corrected dose, the processor 12 is configured to calculate SUVs. The SUV at one or more locations are calculated by normalizing the activity concentration with the corrected dose. The resulting SUVs have less variability due to the system and/or dose, so more likely represent changes in metabolic function of the patient.

The detected emission events, other functional information, or other scan data is stored in the memory 14. The data is stored in any format. The memory 14 is a buffer, cache, RAM, removable media, hard drive, magnetic, optical, database, or other now known or later developed memory. The memory 14 is a single device or group of two or more devices. The memory 14 is part of SPECT scanner 10 or a remote workstation or database, such as a PACS memory.

The memory 14 may store data at different stages of processing, such as counts, time to reach a count, raw data representing detected events without further processing, filtered or thresholded data prior to reconstruction, reconstructed data, filtered reconstruction data, system matrix, projection data, thresholds, an image to be displayed, an already displayed image, or other data. The memory 14 or a different memory stores class standard sensitivities loaded into or provided to the SPECT scanner 10. The memory 14 or a different memory stores the cross-calibration factor and/or any of the sensitivities. For processing, the data bypasses the memory 14, is temporarily stored in the memory 14, or is loaded from the memory 14.

The memory 17 is additionally or alternatively a non-transitory computer readable storage medium with processing instructions. The memory 14 stores data representing instructions executable by the programmed processor 12. The instructions for implementing the processes, methods and/or techniques discussed herein are provided on non-transitory computer-readable storage media or memories, such as a cache, buffer, RAM, removable media, hard drive or other computer readable storage media. Computer readable storage media include various types of volatile and nonvolatile storage media. The functions, acts or tasks illustrated in the figures or described herein are executed in response to one or more sets of instructions stored in or on computer readable storage media. The functions, acts or tasks are independent of the particular type of instructions set, storage media, processor or processing strategy and may be performed by software, hardware, integrated circuits, firmware, micro code and the like, operating alone or in combination. Likewise, processing strategies may include multiprocessing, multitasking, parallel processing and the like. In one embodiment, the instructions are stored on a removable media device for reading by local or remote systems. In other embodiments, the instructions are stored in a remote location for transfer through a computer network or over telephone lines. In yet other embodiments, the instructions are stored within a given computer, CPU, GPU, or system.

The display 16 is a CRT, LCD, plasma screen, projector, printer, or other output device for showing an image. The display 16 displays an image of the reconstructed functional volume, such as showing activity concentration as a function of location. The uptake function of the tissues of the patient is represented in the image. Multiplanar reconstruction, 3D rendering, or cross-section imaging may be used to generate the image from the voxels of the reconstructed volume. Alternatively or additionally, any quantities derived by the processor 12 may be displayed, such as SUVs and/or change in SUV. Other quantities may be determined, such as average SUV or activity concentration for a region, maximum SUV, peak SUV in a predetermined unit volume, variance in activity concentration, or total SUV.

While the invention has been described above by reference to various embodiments, it should be understood that many changes and modifications can be made without departing from the scope of the invention. It is therefore intended that the foregoing detailed description be regarded as illustrative rather than limiting, and that it be understood that it is the following claims, including all equivalents, that are intended to define the spirit and scope of this invention.

I claim:

1. In a non-transitory computer readable storage medium having stored therein data representing instructions executable by a programmed processor for cross-calibration in single photon emission computed tomography (SPECT), the storage medium comprising instructions for:
    measuring a system specific sensitivity of a camera to a long-lived point source;
    estimating activity concentration in SPECT as a function of the system specific sensitivity;
    correcting an injected dose value as a function of the system specific sensitivity, wherein correcting comprises correcting the injected dose value for a radiotracer used in a patient with a cross-calibration value, the cross-calibration value being a function of a system specific sensitivity to a patient specific radiotracer calculated from the system specific sensitivity to the long-lived point source and a dose calibrator referenced radiotracer sensitivity; and
    calculating a specific uptake value from the activity concentration and the corrected injected dose value.

2. The non-transitory computer readable storage medium of claim 1 wherein measuring comprises measuring with the camera the system specific sensitivity to the long-lived point source comprising a factory calibrated point source of a known dose.

3. The non-transitory computer readable storage medium of claim 1 wherein estimating comprises estimating, by reconstruction, with a system specific sensitivity to a patient specific radiotracer calculated from the system specific sensitivity to the long-lived point source.

4. The non-transitory computer readable storage medium of claim 1 wherein calculating comprises dividing the activity concentration by the corrected injected dose value.

5. In a non-transitory computer readable storage medium having stored therein data representing instructions executable by a programmed processor for cross-calibration in single photon emission computed tomography (SPECT), the storage medium comprising instructions for:
    measuring a system specific sensitivity of a camera to a long-lived point source;
    estimating activity concentration in SPECT as a function of the system specific sensitivity;
    correcting an injected dose value as a function of the system specific sensitivity; and
    calculating a specific uptake value from the activity concentration and the corrected injected dose value, wherein calculating comprises dividing the activity concentration by the corrected injected dose value.

6. The non-transitory computer readable storage medium of claim 5 wherein measuring comprises measuring with the camera the system specific sensitivity to the long-lived point source comprising a factory calibrated point source of a known dose.

7. The non-transitory computer readable storage medium of claim 5 wherein estimating comprises estimating, by reconstruction, with a system specific sensitivity to a patient specific radiotracer calculated from the system specific sensitivity to the long-lived point source.

8. The non-transitory computer readable storage medium of claim 5 wherein correcting comprises correcting the injected dose value for a radiotracer used in a patient with a cross-calibration value, the cross-calibration value being a function of a system specific sensitivity to a patient specific radiotracer calculated from the system specific sensitivity to the long-lived point source and a dose calibrator referenced radiotracer sensitivity.

* * * * *